(12) United States Patent
Gante et al.

(10) Patent No.: US 6,204,280 B1
(45) Date of Patent: Mar. 20, 2001

(54) ADHESION RECEPTOR ANTAGONISTS

(75) Inventors: Joachim Gante, Darmstadt; Horst Juraszyk; Peter Raddatz, both of Seeheim; Hanns Wurziger, Darmstadt; Sabine Bernotat-Danielowski, Bad Nauheim; Guido Melzer, Hofheim/Ts.; Matthias Wiesner, Mainz; Claus Fittschen, Fr.-Crumbach, all of (DE)

(73) Assignee: Merck Patent Gesellschaft mit berschrankter Haftung (DE)

( * ) Notice: Subject to any disclaimer, the term of this patent is extended or adjusted under 35 U.S.C. 154(b) by 0 days.

(21) Appl. No.: 09/163,481

(22) Filed: Sep. 30, 1998

Related U.S. Application Data

(62) Division of application No. 08/552,206, filed on Nov. 2, 1995.

(30) Foreign Application Priority Data

Nov. 2, 1994 (DE) .................................................. 44 39 110
Mar. 16, 1995 (DE) .............................................. 195 09 093

(51) Int. Cl.[7] ........................ C07D 263/24; A61K 31/421
(52) U.S. Cl. ............................................. 514/376; 548/232
(58) Field of Search ............................... 548/232; 514/376

(56) References Cited

U.S. PATENT DOCUMENTS

| 5,480,899 | * | 1/1996 | Yano et al. | 514/326 |
| 5,561,145 | * | 10/1996 | Prucher | 514/326 |
| 5,561,148 | * | 10/1996 | Gante et al. | 514/326 |
| 5,776,937 | * | 7/1998 | Gante et al. | 514/252 |

FOREIGN PATENT DOCUMENTS

| 0 086 403 | 8/1983 | (EP) . |
| 0 381 033 | 8/1989 | (EP) . |
| 0 352 781 | 1/1990 | (EP) . |
| 0 459 256 | 12/1991 | (EP) . |
| 0 462 960 | 12/1991 | (EP) . |
| 0 511 031 | 10/1992 | (EP) . |
| 0 605 729 | 7/1994 | (EP) . |
| 834968 | 5/1960 | (GB) . |

OTHER PUBLICATIONS

Born, Nature, 4832:927–929 (Jun. 9, 1962).
Smith et al., J. Biol. Chem., 265(21):12267–12271 (1990).
Valentin–Weigand et al., Infection and Immunity, 56(11):2851–2855 (Nov. 1988).

* cited by examiner

*Primary Examiner*—John M. Ford
(74) *Attorney, Agent, or Firm*—Millen. White, Zelano & Branigan, P.C.

(57) ABSTRACT

Compounds of the formula I

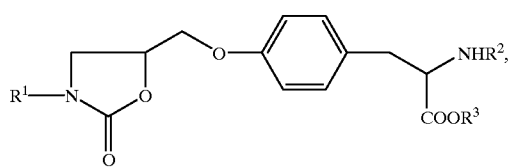

wherein $R^1$, $R^2$ and $R^3$ have the meanings defined herein, and also their physiologically acceptable salts, inhibit the binding of fibrinogen to the corresponding receptor and can be employed for the treatment of thromboses, osteoporoses, oncoses, apoplexy, cardiac infarct, ischaemias, inflammations, arteriosclerosis and osteolytic disorders.

8 Claims, No Drawings

ADHESION RECEPTOR ANTAGONISTS

This is a division, of application Ser. No. 08/552,206 filed Nov. 2, 1995.

SUMMARY OF THE INVENTION

The invention relates to novel oxazolidinone derivatives of the formula I

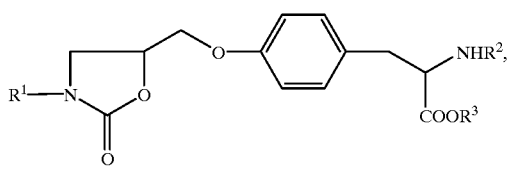

wherein

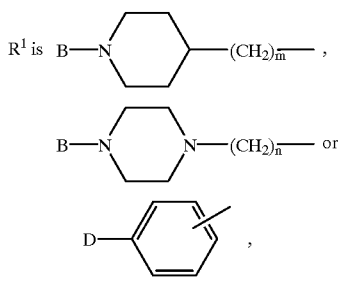

$R^2$ is H, A, Ac, A—$SO_2$—, Ar—$SO_2$— or a conventional amino protective group, $R^3$ is H, A, cycloalkyl having 3 to 7 C atoms, Ar or Ar—$(CH_2)_k$—, A is alkyl having 1 to 16 C atoms, B is H, A or $H_2N$—C(=NH)—, D is $H_2N$—$CH_2$—, $H_2N$—C(=NH)— or $H_2N$—C(=NH)—NH—$CH_2$—, where the primary amino groups can also be provided with conventional amino protective groups, Ac is alkanoyl having 1 to 10 C atoms or aroyl having 7 to 11 C atoms, Ar is phenyl which is unsubstituted or mono- or disubstituted by A, Cl, Br, I, OA, OH, $NO_2$, CN, $NH_2$, NHA and/or $NA_2$, or benzyl, m is 0, 1, 2, 3 or 4, n is 2, 3 or 4 and k is 1, 2, 3 or 4, and their physiologically acceptable salts.

Similar compounds are disclosed in EP-A1-0 381 033.

An object of the invention is to provide novel compounds having useful properties, in particular those which can be used for the production of medicaments.

Upon further study of the specification and appended claims, further objects and advantages of this invention will become apparent to those skilled in the art.

These objects are achieved by the invention. It was found that the compounds of the formula I, and their solvates and salts, have useful pharmacological properties together with good tolerability. The compounds have integrin inhibiting effects, in particular they inhibit interaction of $\beta_3$- or $\beta_5$-integrin receptors with ligands. Especially, they affect the $a_v\beta_3$, $a_v\beta_5$ and $a_{IIb}\beta_3$ integrins. The activity of the compounds can be demonstrated, for example, by the method of J. W. Smith et al., described in J. Biol. Chem. 265:12267–12271 (1990). In particular, they inhibit the binding of fibrinogen, fibronectin and of the von Willebrand factor to the fibrinogen receptor of the blood platelets (glycoprotein IIb/IIIa) and also the binding thereof and of further adhesive proteins, such as vitronectin, collagen and laminin, to the corresponding receptors on the surface of various cell types. The compounds thus affect cell-cell and cell-matrix interactions. In particular, they prevent the formation of blood platelet thrombi and can therefore be used for the treatment of thromboses, apoplexia, cardiac infarct, angina pectoris, osteolytic diseases, in particular osteoporosis, antiangiogenesis and restenosis after angioplasty, ischaemias, inflammations, arteriosclerosis and of acute kidney failure. The compounds also have an effect on tumor cells by inhibiting their metastasization. They can thus also be employed as antitumor agents.

There are indications that tumor cells pass into the vessels by means of microthrombi and are thus protected from detection by cells of the immune system. Microthrombi also have a supportive effect on the binding of tumor cells to the vessel walls. Since the formation of the microthrombi is connected with the fibrinogen binding to the fibrinogen receptor (glycoprotein IIb/IIIa), fibrinogen binding inhibitors likewise count as metastasis inhibitors.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitor can be labeled with a signal generating or detectable moiety.

The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

The compounds are additionally suitable as antimicrobial agents which can prevent infections, such as can be caused, for example, by bacteria, fungi or yeasts. The substances can therefore preferably be given as accompanying antimicrobial agents when operations on bodies are performed in which exogenous substances, such as biomaterials, implants, catheters or cardiac pacemakers, are employed. They act as antiseptics. Antimicrobial activities of the compounds can be demonstrated, for example, by the method of P. Valentin-Weigand et al., described in Infection and Immunity, 2851–2855 (1988).

The other properties of the compounds can be demonstrated by methods which are described in EP-A1-0 462 960. The inhibition of fibrin binding to the fibrinogen receptor can be demonstrated by the method which is indicated in EP-A1-0 381 033. The platelet aggregation-inhibiting action can be demonstrated in vitro by the method of Born (Nature, 4832:927–929 (1962)).

The invention also relates to a process for the preparation of a compound of the formula I indicated, and of its salts, characterized in that (a) a compound of the formula I is liberated from one of its functional derivatives by treating with a solvolyzing or hydrogenolyzing agent, or in that (b) a compound of the formula II

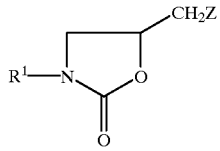

wherein
z is Cl, Br, I, OH or a reactive esterified OH group, and
R$^1$ has the meaning indicated above,
is reacted with a compound of the formula III

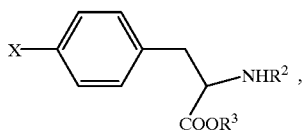

wherein
R$^2$ and R$^3$ have the meanings indicated and
X is OH or a salt-like radical derivable from OH,
or in that (c) a compound of the formula IV

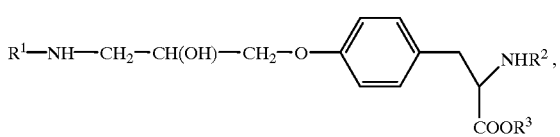

wherein
R$^1$, R$^2$ and R$^3$ have the meanings indicated,
is reacted with a reactive derivative of carbonic acid, or in that (d) a compound of the formula V

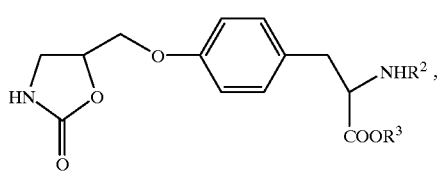

where
R$^2$ and R$^3$ have the meanings indicated, is reacted with a compound of the formula VI

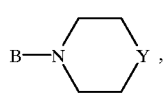

wherein
B has the meaning indicated and

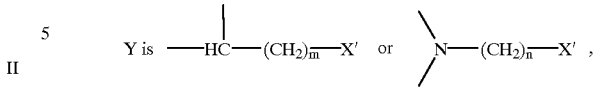

wherein
m and n have the meanings already indicated and
X' is Cl, Br, I or another, easily nucleophilically displaceable leaving group,
or in that e) for the preparation of a guanidinomethyl compound of the formula I (R$^1$=a phenyl radical monosubstituted by H$_2$N—C(=NH)—NH—CH$_2$—), an amino compound corresponding to the formula I, but which instead of the radical R$^1$ contains an aminomethylphenyl group, is treated with an amidinating agent, or in that (f) a radical R$^3$ is converted into another radical R$^3$ by hydrolyzing an ester of the formula I, or by esterifying a carboxylic acid of the formula I, or in that (g) (a) radical(s) R$^1$ and/or R$^2$ is (are) converted into (a) other radical(s) R$^1$ and/or R$^2$, and/or in that (h) a compound of the formula I is converted into one of its salts by treating with an acid or base.

The compounds of the formula I have at least one chiral center and can therefore occur in several enantiomeric forms. All these forms (e.g. D- and L-forms) and their mixtures (e.g. the DL-forms) are included in the formula I.

Hereinbefore and hereinafter, the radicals or parameters A, B, D, X, Y, Z, R$^1$ to R$^3$, Ac, Ar, k, m and n have the meanings indicated in the formulae I to VI if not expressly stated otherwise. If several groups designated as identical are present in the molecule, they can assume various definitions independently of one another.

In the above formulae, the group A has 1–6, preferably 1, 2, 3 or 4, C atoms. Specifically, A is preferably methyl, ethyl, propyl, isopropyl, butyl, isobutyl, sec-butyl or tert-butyl, and also pentyl, 1-,2- or 3-methylbutyl, 1,1-, 1,2- or 2,2-dimethylpropyl, 1-ethylpropyl, hexyl, or 1-, 2-, 3- or 4-methylpentyl.

R$^1$ is preferably a phenyl radical substituted in the 4-position, but also substituted in the 2- or 3-position as indicated, specifically preferably 2-, 3- or (in particular) 4-aminomethylphenyl, 2-, 3- or (in particular) 4-amidinophenyl, 2-, 3- or 4-guanidinomethylphenyl, where in all cases the primary amino groups can also be provided with conventional amino protective groups. R$^1$ is also preferably a 4-piperidyl, 4-piperidylmethyl, 4-piperidylethyl, 1-amidino-4-piperidyl, 1-amidino-4-piperidylmethyl, 4-piperazinylethyl, 4-piperazinylpropyl, 4-piperazinylbutyl, 1-amidino-4-piperazinylethyl or 1-amidino-4-piperazinylpropyl radical.

R$^2$ is preferably hydrogen, methyl, ethyl, methyl-, ethyl-, n-propyl- or n-butylsulfonyl, toluene-sulfonyl or a conventional amino protective group.

R$^3$ is preferably hydrogen, methyl or ethyl.

Ar is preferably unsubstituted phenyl or 4-methylphenyl, Ac is preferably alkanoyl having 1–6 C atoms, such as formyl, acetyl, propionyl, butyryl, isobutyryl, valeryl or caproyl, and also benzoyl, toluyl, 1- or 2-naphthoyl or phenylacetyl.

The parameter m is preferably 0 or 1, whereas the parameter k is preferably 1. The parameter n is preferably 2 or 3.

Among the compounds of the formula I, those are preferred in which at least one of the radicals, groups and/or parameters indicated has one of the preferred meanings indicated. Some groups of preferred compounds are those of the formulae Ia to If, which correspond to the formula I, but wherein in Ia $R^1$ is amidinophenyl;

in Ib $R^1$ is amidinophenyl and $R^2$ is hydrogen;

in Ic $R^1$ is aminomethylphenyl and $R^3$ is hydrogen or methyl;

Id $R^1$ is amidinophenyl and $R^3$ is hydrogen or methyl;

Ie $R^1$ is piperidylmethyl or piperidylethyl and $R^2$ is hydrogen or A—$SO_2$—;

If $R^3$ is 1-amidinopiperidylmethyl and $R^2$ is hydrogen or A—$SO_2$—;

Ig $R^1$ is piperazinoethyl or -propyl and $R^2$ is hydrogen or A—$SO_2$—;

Ih $R^1$ is 1-amidinopiperazinoethyl or -propyl and $R^2$ is hydrogen or A—$SO_2$—.

The compounds of the formula I and also the starting substances for their preparation are otherwise prepared by methods known per se, such as are described in the literature (e.g. in the standard works such as Houben-Weyl, Methoden der organischen Chemie, [Methods of organic chemistry], Georg-Thieme-Verlag, Stuttgart; and also EP-A1-0 381 033, EP-A1-0 462 960), namely under reaction conditions which are known and suitable for the reactions mentioned. Use can also be made in this case of variants which are known per se, but not mentioned here in greater detail.

The starting substances can also be formed in situ, if desired, such that they are not isolated from the reaction mixture, but immediately reacted further to give the compounds of the formula I.

The compounds of the formula I can be obtained by liberating them from their functional derivatives by solvolysis, in particular hydrolysis, or by hydrogenolysis.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which, instead of an H atom which is bonded to an N atom, carry an amino protective group, in particular those which, instead of an EN group, carry an R'-N group wherein R' is an amino protective group, and/or those which, instead of the H atom of a hydroxyl group, carry a hydroxy protective group, e.g. those which correspond to the formula I but instead of a group —COOH carry a group —COOR" wherein R" is a hydroxyl protective group.

Several—identical or different—protected amino and/or hydroxyl groups can also be present in the molecule of the starting substance. If the protective groups present are different from one another, they can be selectively removed in many cases.

The expression "amino protective group" is generally known and relates to groups which are suitable for protecting (for blocking) an amino group from chemical reactions, but which are easily removable after the desired chemical reaction has been carried out in another position of the molecule. Typical groups of this type are, in particular, unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl, triphenylmethyl). Since the amino protective groups are removed after the desired reaction (or reaction sequence), their nature and size is otherwise not critical; but those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids, and also, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC), 2-iodoethoxycarbonyl; aralkyloxycarbonyl such as benzyloxycarbonyl (CBZ), 4-methoxybenzyloxycarbonyl and 9-fluorenylmethoxycarbonyl (FMOC). Preferred amino protective groups are BOC, DNP and BOM, and also CBZ, benzyl and acetyl.

The expression "hydroxyl protective group" is likewise generally known and relates to groups which are suitable for protecting a hydroxyl group from chemical reactions, but which are easily removable after the desired chemical reaction has been carried out in another position of the molecule. Typical groups of this type are the abovementioned unsubstituted or substituted aryl, aralkyl or acyl groups, and also alkyl groups. The nature and size of the hydroxyl protective groups is not critical, since they are removed again after the desired chemical reaction or reaction sequence; groups having 1–20, in particular 1–10, C atoms are preferred. Examples of hydroxyl protective groups are, inter alia, tert-butyl, benzyl, p-nitrobenzoyl, p-toluenesulfonyl and acetyl, benzyl and acetyl being particularly preferred.

The functional derivatives of the compounds of the formula I to be used as starting substances can be prepared by customary methods, such as are described, for example, in the standard works and patent applications mentioned, e.g. by reaction of compounds which correspond to the formulae II and III, but where at least one of these compounds contains a protective group instead of an H atom.

The liberation of the compounds of the formula I from their functional derivatives takes place—depending on the protective group used—using, for example, strong acids, expediently using trifluoroacetic acid or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary.

Suitable inert solvents are preferably organic acids, e.g. carboxylic acids such as acetic acid, ethers such as tetrahydrofuran or dioxane, amides such as dimethylformamide (DMF), halogenated hydrocarbons such as dichloromethane, sulfoxides such as dimethyl sulfoxide (DMSO), and also alcohols such as methanol, ethanol or isopropanol as well as water. Mixtures of the abovementioned solvents are also suitable. Trifluoroacetic acid is preferably used in an excess without addition of a further solvent; perchloric acid in the form of a mixture of acetic acid and 70% perchloric acid in the ratio 9:1. The reaction temperatures for the cleavage are expediently about 0–50°; preferably reaction is carried out at about 15–30° (room temperature).

The BOC group can be removed, for example, preferably using 40% trifluoroacetic acid in dichloromethane or using approximately 3 to 5 N HCl in dioxane at preferably about 15–60°, the FMOC group using an approximately 5–20% solution of dimethylamine, diethylamine or piperidine in DMF at preferably about 15–50°. Removal of the DNP group is carried out, for example, also using an approximately 3–10% solution of 2-mercaptoethanol in DMF/water at preferably about 15–30°.

Hydrogenolytically removable protective groups (e.g., BOM, CBZ or benzyl) can be removed, for example, by treating with hydrogen in the presence of a catalyst (e.g., of a noble metal catalyst such as palladium, expediently on a support such as carbon). Suitable solvents in this case are those indicated above, in particular, for example, alcohols such as methanol or ethanol or amides such as DMF. As a rule, the hydrogenolysis is carried out at temperatures of preferably about 0–100° and pressures of preferably about 1–200 bar, especially about 20–30° and about 1–10 bar. A hydrogenolysis of the CBZ group readily takes place, for example, on 5–10% Pd-C in methanol at preferably about 20–30°.

Compounds of the formula I can preferably also be obtained by reaction of a compound of the formula II with a phenol derivative of the formula III. In this case, use is expediently made of the methods which are known per se for the preparation of ethers.

The leaving group Z is preferably Cl, Br, I, $C_1$–$C_6$-alkylsulfonyloxy such as methane- or ethanesulfonyloxy or $C_6$–$C_{10}$-arylsulfonyloxy such as benzene-, p-toluene- or 1- or 2-naphthalenesulfonyloxy.

The reaction preferably takes place in the presence of an additional base, e.g. of an alkali metal or alkaline earth metal hydroxide or carbonate such as sodium, potassium or calcium hydroxide, sodium, potassium or calcium carbonate, in an inert solvent, e.g. a halogenated hydrocarbon such as dichloromethane, an ether such as THF or dioxane, an amide such as DMF or dimethylacetamide, or a nitrile such as acetonitrile, at temperatures of preferably about –10 to 200°, especially 0–120°. If the leaving group Z is different from I, an addition of an iodide such as potassium iodide is recommended.

As a rule, the starting substances of the formula II are new. They can be prepared, for example, by reaction of a substituted aniline of the formula $R^1$—$NH_2$ with a compound of the formula $R^5CH_2$—$CHR^6$—$CH_2OH$ (wherein $R^5$ is Z, $R^6$ is OH or $R^5$ and $R^6$ together are also O) to give a compound of the formula $R^1$—NH—$CH_2$—$CHR^8$—$CH_2OH$ (wherein $R^8$ is OH), reaction with a derivative of carbonic acid such as diethyl carbonate to give 3-$R^1$-5-hydroxymethyl-2-oxazolidinones and, if appropriate, conversion of the hydroxymethyl group to a $CH_2Z$ group, e.g. using $SOCl_2$, $SoBr_2$, methanesulfonyl chloride or p-toluenesulfonyl chloride. As a rule, the compounds of the formula III are known or can be prepared from suitable phenol derivatives or from phenol in analogy to known compounds.

Compounds of the formula I can also be obtained by reaction of a compound of the formula IV (or of a reactive derivative thereof) with a reactive derivative of carbonic acid.

Suitable carbonic acid derivatives are, in particular, dialkyl carbonates such as diethyl carbonate, and also alkyl chloroformates such as ethyl chloroformate. The carbonic acid derivative, which is expediently employed in an excess, is preferably also used as a solvent or suspending agent. However, one of the solvents indicated can also be present if it is inert in this reaction. The addition of a base is furthermore recommended, in particular of an alkali metal alkoxide such as potassium tert-butoxide. The reaction is expediently carried out at reaction temperatures of preferably about 0–150°, especially 70–120°.

As a rule, the starting substances of the formula IV are novel. They are obtainable, for example, by functionalization of the abovementioned compounds of the formula $R^1$—NH—$CH_2$—CH(OH)—$CH_2OH$ to give compounds of the formula $R^1$—NH—$CH_2$—CH(OH)—$CH_2$—Z and reaction with compounds of the formula III.

For the preparation of compounds of the formula I wherein $R^1$ is a guanidinophenyl group, a corresponding aminophenyl compound can be treated with an amidinating agent. The preferred amidinating agent is 1-amidino-3,5-dimethylpyrazole, which is employed, in particular, in the form of its nitrate The reaction is expediently carried out with addition of a base such as triethylamine or ethyldiisopropylamine in an inert solvent or solvent mixture, e.g. water/dioxane at temperatures of preferably about 0–120°, especially 60–120°.

It is furthermore possible to convert a radical $R^3$ into another radical $R^3$ in a compound of the formula I by hydrolyzing an ester of the formula I or esterifying a carboxylic acid of the formula I.

For the esterification, an acid of the formula I ($R^3$=H) can be treated with an excess of an alcohol of the formula $R^3$—OH ($R^3$=A or benzyl), expediently in the presence of a strong acid such as hydrochloric acid or sulfuric acid at temperatures of preferably about 0–100, especially 20–50°.

Conversely, an ester of the formula I ($R^3$=A or benzyl) can be converted into the corresponding acid of the formula I ($R^3$=H), expediently by solvolysis or hydrogenolysis according to one of the methods indicated above, e.g. using NaOH or KOH in water/dioxane at temperatures of preferably about 0–40°, especially 10–30°.

It is also possible to convert a radical $R^1$ and/or $R^2$ into another radical $R^1$ and/or $R^2$.

In particular, primary or secondary amino groups can be alkylated, acylated, amidinated or provided with conventional amino protective groups or alkyl- or arylsulfonyl groups or, conversely, liberated by removal of these groups.

For the preparation of an amidine of the formula I ($R^1$=amidinophenyl), ammonia can be added to a nitrile of the formula I ($R^1$=cyanophenyl). The addition preferably takes place in several steps in that, in a manner known per se, a) the nitrile is converted using $H_2S$ into a thioamide, which is converted using an alkylating agent, e.g. $CH_3I$, into the corresponding S-alkyl imidothioester, which for its part reacts with $NH_3$ to give the amidine, b) the nitrile is converted using an alcohol, e.g. ethanol in the presence of HCl, into the corresponding imidoester and this is treated with ammonia, or c) the nitrile is reacted with lithium bis(trimethylsilyl)amide and the product is then hydrolysed.

Analogously, the corresponding N-hydroxy-amidines of the formula I ($R^1$=phenyl substituted by HO—NH—C(=NH) are obtainable from the nitrites if the reaction is carried out according to a) or b), but using hydroxylamine instead of ammonia. These products can then be further derivatized by reducing them, for example with hydrogen gas.

A base of the formula I can be converted into the associated acid addition salt using an acid. For this reaction, suitable acids are in particular those which yield physiologically acceptable salts. Inorganic acids can thus be used, e.g. sulfuric acid, nitric acid, halohydric acids such as hydrochloric acid or hydrobromic acid, phosphoric acids such as orthophosphoric acid, sulfamic acid, and also organic acids, in particular aliphatic, alicyclic, araliphatic, aromatic or heterocyclic mono- or polybasic carboxylic, sulfonic or sulfuric acids, e.g. formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, e.g. picrates, can be used for the isolation and/or purification of the compounds of the formula I.

If desired, the free bases of the formula I can be liberated from their salts by treatment with strong bases such as sodium or potassium hydroxide, or sodium or potassium carbonate.

It is also possible to convert carboxylic acids of the formula I ($R^3$=H) into their metal or ammonium salts, e.g. their sodium, potassium or calcium salts, by reaction with appropriate bases.

The compounds of the formula I contain one or more chiral centers and can therefore exist in racemic or in optically active form. Racemates which are obtained can be separated into the enantiomers mechanically or chemically by methods known per se. Preferably, diastereomers are formed from the racemic mixture by reaction with an optically active resolving agent. Suitable resolving agents are, for example, optically active acids, such as the D- and L-forms of tartaric acid, diacetyltartaric acid, dibenzoyltartaric acid, mandelic acid, malic acid, lactic acid or the various optically active camphorsulfonic acids such as β-camphorsulfonic acid. Resolution of the enantiomers with the aid of a column packed with an optically active resolving agent (e.g. dinitrobenzoylphenylglycine) is also advantageous; a suitable eluent is, for example, a hexane/isopropanol/acetonitrile mixture, e.g. in the volume ratio 82:15:3.

Of course, it is also possible to obtain optically active compounds of the formula I according to the methods described above by using starting substances (e.g. those of the formula II) which are already optically active.

The novel compounds of the formula I and their physiologically acceptable salts can be used for the production of pharmaceutical preparations by bringing them into a suitable dosage form together with at least one excipient or auxiliary and, if desired, together with one or more further active compounds. The preparations thus obtained can be employed as medicaments in human or veterinary medicine. Suitable vehicles are organic or inorganic substances which are suitable for enteral (e.g. oral or rectal) or parenteral administration or for administration in the form of an inhalation spray and do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc or cellulose. For oral administration, tablets, coated tablets, capsules, syrups, juices or drops are used in particular; coated tablets and capsules having enteric coatings or capsule shells are especially of interest. For rectal administration, suppositories are used and for parenteral administration solutions, preferably oily or aqueous solutions, and also suspensions, emulsions or implants.

For administration as an inhalation spray, sprays can be used which contain the active compound either dissolved or suspended in a propellant mixture. The active compound is expediently used in this case in micronized form, it being possible for one or more additional physiologically tolerable solvents to be present, e.g., ethanol. Inhalation solutions can be administered with the aid of customary inhalers. The novel compounds can also be lyophilized and the lyophilizates obtained used, for example, for the production of injection preparations. The preparations indicated can be sterilized and/or contain auxiliaries such as preservatives, stabilizers and/or wetting agents, emulsifiers, salts for affecting the osmotic pressure, buffer substances, colorants and/or aromatic substances. If desired, they can also contain one or more further active compounds, e.g., one or more vitamins.

As a rule, the substances according to the invention are administered in analogy to other known, commercially available pharmaceuticals, but in particular in analogy to the compounds described in EP-A-459 256, preferably in doses of about 5 mg–1 g, especially about 50–500 mg per dosage unit. The daily dose is preferably about 0.1–20 mg/kg, especially about 1–10 mg/kg, of body weight. The specific dose for each intended patient depends, however, on all sorts of factors, for example, on the activity of the specific compound employed, on the age, body weight, general state of health, sex, on the diet, on the time and route of administration, on the excretion rate, pharmaceutical substance combination and severity of the particular disorder to which the therapy applies. Oral administration is preferred.

Suitable preparations for using the compounds as antimicrobial agents are, for example, injection vials, ampoules, solutions and capsules. Carriers, excipients and further additives are mentioned in Examples A–H. The amount of the inventive compound in the antimicrobial agents is preferably about 0.05–500 mg/dosage unit.

Hereinbefore and hereinafter all temperatures are indicated in ° C. In the following examples, "customary working up" means: water is added, if necessary, the mixture is adjusted, depending on the constitution of the final product, to a pH of between 0 and 8 and filtered through an ion exchange column, the organic phase is dried over sodium sulfate, evaporated and lyophilized if appropriate, and the product is purified by chromatography on silica gel and/or crystallization. In the following examples, "4-piperidylethyl" always means "2-(4-piperidyl)ethyl," "4-piperidylpropyl" always means "3-(4-piperidyl)propyl" and "4-piperidylbutyl" always means "4-(4-piperidyl)butyl." Likewise, "4-piperazinylethyl" always means "2-(4-piperazinyl)ethyl," "4-piperazinylpropyl" always means "3-(4-piperazinyl)propyl" and "4-piperazinylbutyl" always means "4-(4-piperazinyl)butyl." The derivatives provided with protective groups are also included in this case, e.g., the BOC-protected compounds.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, unless otherwise indicated, all parts and percentages are by weight.

The entire disclosure of all applications, patents and publications, cited above and below, and of corresponding German applications P 44 39 110.2, filed Nov. 2, 1994, and DE 1 95 09 093.4, filed Mar. 16, 1995, are hereby incorporated by reference.

EXAMPLES

Example 1

One equivalent of NaH is added to a solution of 1.9 g of methyl 2-N-BOC-amino-3-(4-hydroxyphenyl)propanoate ("A") [obtainable from tyrosine by esterificaton with methanol and introduction of the BOC protective group] in 20 ml of dimethylformamide (DMF) and the mixture is stirred for 30 min at room temperature. 1.8 g of 3-p-N-BOC-amidinophenyl-5-methanesulfonyloxymethyloxazolidin-2-one [obtainable by reaction of p-aminobenzonitrile with 2,3-epoxypropan-1-ol to give p-(N-2,3-dihydroxypropylamino)benzonitrile, reaction with diethyl carbonate in the presence of K tert-butoxide to give 3-p-cyanophenyl-5-hydroxymethyloxazolidin-2-one, reaction with H$_2$S, methyl iodide and ammonium acetate to give the amidine, introduction of a BOC protective group on the amidine and subsequent esterification with methanesulfonyl chloride], dissolved in 10 ml of DMF, are then added and the mixture is again stirred for 15 min at room temperature. After removal of the solvent and customary working up, 3-p-BOC-amidinophenyl-5-[p-(2-methoxycarbonyl-2-N-BOC-aminoethyl)phenoxy]methyloxazolidin-2-one is obtained.

The following are obtained analogously by reaction of "A"

with 3-(4-N-BOC-piperidyl)-5-methanesulfonyloxymethyloxazolidin-2-one
   3-(4-N-BOC-piperidyl)-5-[p-(2-methoxycarbonyl-2-N-BOC-aminoethyl)phenoxy]methyloxazolidin-2-one;

with 3-(4-N-BOC-piperidylmethyl)-5-methanesulfonyloxymethyloxazolidin-2-one
   3-(4-N-BOC-piperidylmethyl)-5-[p-(2-methoxycarbonyl-2-N-BOC-aminoethyl)phenoxy]methyloxazolidin-2-one;

with 3-(4-N-BOC-piperidylethyl)-5-methanesulfonyloxymethyloxazolidin-2-one
   3-(4-N-BOC-piperidylethyl)-5-[p-(2-methoxycarbonyl-2-N-BOC-aminoethyl)phenoxy]methyloxazolidin-2-one;

with 3-(4-N-BOC-piperidylpropyl)-5-methanesulfonyloxymethyloxazolidin-2-one
   3-(4-N-BOC-piperidylpropyl)-5-[p-(2-methoxycarbonyl-2-N-BOC-aminoethyl)phenoxy]methyloxazolidin-2-one;

with 3-(4-N-BOC-piperidylbutyl)-5-methanesulfonyloxymethyloxazolidin-2-one
   3-(4-N-BOC-piperidylbutyl)-5-[p-(2-methoxycarbonyl-2-N-BOC-aminoethyl)phenoxy]methyloxazolidin-2-one;

with 3-(1-N-BOC-amidino-4-piperidyl)-5-methanesulfonyloxymethyloxazolidin-2-one
   3-(1-N-BOC-amidino-4-piperidyl)-5-[p-(2-methoxycarbonyl-2-N-BOC-aminoethyl)phenoxy]methyloxazolidin-2-one;

with 3-(1-N-BOC-amidino-4-piperidylmethyl)-5-methanesulfonyloxymethyloxazolidin-2-one
   3-(1-N-BOC-amidino-4-piperidylmethyl)-5-[p-(2-methoxycarbonyl-2-N-BOC-aminoethyl)phenoxy]methyloxazolidin-2-one;

with 3-(1-N-BOC-amidino-4-piperidylethyl)-5-methanesulfonyloxymethyloxazolidin-2-one
   3-(1-N-BOC-amidino-4-piperidylethyl)-5-[p-(2-methoxycarbonyl-2-N-BOC-aminoethyl)phenoxy]methyloxazolidin-2-one;

with 3-(1-N-BOC-amidino-4-piperidylpropyl)-5-methanesulfonyloxymethyloxazolidin-2-one
   3-(1-N-BOC-amidino-4-piperidylpropyl)-5-[p-(2-methoxycarbonyl-2-N-BOC-aminoethyl)phenoxy]methyloxazolidin-2-one;

with 3-(1-N-BOC-amidino-4-piperidylbutyl)-5-methanesulfonyloxymethyloxazolidin-2-one
   3-(1-N-BOC-amidino-4-piperidylbutyl)-5-[p-(2-methoxycarbonyl-2-N-BOC-aminoethyl)phenoxy]methyloxazolidin-2-one;

with 3-(1-isopropyl-4-piperidyl)-5-methanesulfonyloxymethyloxazolidin-2-one
   3-(1-isopropyl-4-piperidyl)-5-[p-(2-methoxycarbonyl-2-N-BOC-aminoethyl)phenoxy]methyloxazolidin-2-one;

with 3-(1-methyl-4-piperidylmethyl)-5-methanesulfonyloxymethyloxazolidin-2-one
   3-(1-methyl-4-piperidylmethyl)-5-[p-(2-methoxycarbonyl-2-N-BOC-aminoethyl)phenoxy]methyloxazolidin-2-one;

with 3-(4-N-BOC-piperazinylethyl)-5-methanesulfonyloxymethyloxazolidin-2-one
   3-(4-N-BOC-piperazinylethyl)-5-[p-(2-methoxycarbonyl-2-N-BOC-aminoethyl)phenoxy]methyloxazolidin-2-one;

with 3-(4-N-BOC-piperazinylpropyl)-5-methanesulfonyloxymethyloxazolidin-2-one
   3-(4-N-BOC-piperazinylpropyl)-5-[p-(2-methoxycarbonyl-2-N-BOC-aminoethyl)phenoxy]methyloxazolidin-2-one;

with 3-(4-N-BOC-piperazinylbutyl)-5-methanesulfonyloxymethyloxazolidin-2-one
   3-(4-N-BOC-piperazinylbutyl)-5-[p-(2-methoxycarbonyl-2-N-BOC-aminoethyl)phenoxy]methyloxazolidin-2-one;

with 3-(1-N-BOC-amidino-4-piperazinylethyl)-5-methanesulfonyloxymethyloxazolidin-2-one
   3-(1-N-BOC-amidino-4-piperazinylethyl)-5-[p-(2-methoxycarbonyl-2-N-BOC-aminoethyl)phenoxy]methyloxazolidin-2-one;

with 3-(1-N-BOC-amidino-4-piperazinylpropyl)-5-methane-sulfonyloxymethyloxazolidin-2-one
   3-(1-N-BOC-amidino-4-piperazinylpropyl)-5-[p-(2-methoxycarbonyl-2-N-BOC-aminoethyl)phenoxy]methyloxazolidin-2-one;

with 3-(1-N-BOC-amidino-4-piperazinylbutyl)-5-methanesulfonyloxymethyloxazolidin-2-one
   3-(1-N-BOC-amidino-4-piperazinylbutyl)-5-[p-(2-methoxycarbonyl-2-N-BOC-aminoethyl)phenoxy]methyloxazolidin-2-one;

Example 2

A solution of 0.9 g of 3-p-cyanophenyl-5-[p-(2-methoxycarbonyl-2-N-BOC-aminoethyl)phenoxy]methyloxazolidin-2-one [obtainable according to Ex. 1 by reaction of methyl 2-N-BOC-amino-3-(4-hydroxyphenyl)propanoate with 3-p-cyanophenyl-5-methanesulfonyloxymethyloxazolidin-2-one] in 40 ml of 10% methanolic NH$_3$ solution is hydrogenated on 0.6 g of Raney Ni at room temperature and 1 bar until absorption of H$_2$ has ended. After filtering and evaporating, customary working up gives 3-p-aminomethylphenyl-5-[p-(2-methoxycarbonyl-2-N-BOC-aminoethyl)phenoxy]methyloxazolidin-2-one.

The following are obtained analogously from 3-m-cyanophenyl-5-[p-(2-methoxycarbonyl-2-N-BOC-aminoethyl)phenoxy]methyloxazolidin-2-one
   3-m-aminomethylphenyl-5-[p-(2-methoxycarbonyl-2-N-BOC-aminoethyl)phenoxy]methyloxazolidin-2-one;

from 3-m-cyanophenyl-5-[p-(2-methoxycarbonyl-2-N-butyl-sulfonylaminoethyl)phenoxy]methyloxazolidin-2-one
   3-m-aminomethylphenyl-5-[p-(2-methoxycarbonyl-2-N-butylsulfonylaminoethyl)phenoxy]methyloxazolidin-2-one;

from 3-p-cyanophenyl-5-[p-(2-methoxycarbonyl-2-N-butylsulfonylaminoethyl)phenoxy]methyloxazolidin-2-one 3-p-aminomethylphenyl-5-[p-(2-methoxycarbonyl-2-N-butylsulfonylaminoethyl)phenoxy]methyloxazolidin-2-one;
from 3-o-cyanophenyl-5-[p-(2-methoxycarbonyl-2-N-butylsulfonylaminoethyl)phenoxy]methyloxazolidin-2-one
3-o-aminomethylphenyl-5-[p-(2-methoxycarbonyl-2-N-butylsulfonylaminoethyl)phenoxy]methyloxazolidin-2-one;
from 3-o-cyanophenyl-5-[p-(2-methoxycarbonyl-2-N-BOC-aminoethyl)phenoxy]methyloxazolidin-2-one
3-o-aminomethylphenyl-5-[p-(2-methoxycarbonyl-2-N-BOC-aminoethyl)phenoxy]methyloxazolidin-2-one;

Example 3

Analogously to Example 1, starting from methyl 2-N-butylsulfonylamino-3-(4-hydroxyphenyl)propanoate ("B") [obtainable from tyrosine by esterification with methanol and reaction with butylsulfonyl chloride] by reaction with 3-(1-N-BOC-amidino-4-piperidyl)-5-methanesulfonyloxymethyloxazolidin-2-one [obtainable by reaction of 1-N-BOC-amidino-4-aminopiperidine with 2,3-epoxypropan-1-ol to give 1-N-BOC-amidino-4-(N-2,3-dihydroxypropylamino)piperidine, reaction with diethyl carbonate in the presence of K tert-butoxide to give 3-(1-N-BOC-amidino-4-piperidyl)-5-hydroxymethyloxazolid-in-2-one and subsequent esterification with methanesulfonyl chloride], 3-[1-N-BOC-amidino-4-piperidyl)-5-[p-(2-methoxycarbonyl-2-N-butylsulfonylaminoethyl)phenoxy]methyloxazolidin-2-one is obtained.

The following are obtained analogously by reaction of "B"
with 3-(4-N-BOC-piperidyl)-5-methanesulfonyloxymethyloxazolidin-2-one
3-(4-N-BOC-piperidyl)-5-[p-(2-methoxycarbonyl-2-N-butylsulfonylaminoethyl)phenoxy]methyloxazolidin-2-one;
with 3-(4-N-BOC-piperidylmethyl)-5-methanesulfonyloxymethyloxazolidin-2-one
3-(4-N-BOC-piperidylmethyl)-5-[p-(2-methoxycarbonyl-2-N-butylsulfonylaminoethyl)phenoxy]methyloxazolidin-2-one;
with 3-(4-N-BOC-piperidylethyl)-5-methanesulfonyloxymethyloxazolidin-2-one
3-(4-N-BOC-piperidylethyl)-5-[p-(2-methoxycarbonyl-2-N-butylsulfonylaminoethyl)phenoxy]methyloxazolidin-2-one;
with 3-(4-N-BOC-piperidylpropyl)-5-methanesulfonyloxymethyloxazolidin-2-one
3-(4-N-BOC-piperidylpropyl)-5-[p-(2-methoxycarbonyl-2-N-butylsulfonylaminoethyl)phenoxy]methyloxazolidin-2-one;
with 3-(4-N-BOC-piperidylbutyl)-5-methanesulfonyloxymethyloxazolidin-2-one
3-(4-N-BOC-piperidylbutyl)-5-[p-(2-methoxycarbonyl-2-N-butylsulfonylaminoethyl)phenoxy]methyloxazolidin-2-one;
with 3-(1-ethyl-4-piperidyl)-5-methanesulfonyloxymethyloxazolidin-2-one
3-(1-ethyl-4-piperidyl)-5-[p-(2-methoxycarbonyl-2-N-butylsulfonylaminoethyl)phenoxy]methyloxazolidin-2-one;
with 3-(1-N-BOC-amidino-4-piperidylmethyl)-5-methanesulfonyloxymethyloxazolidin-2-one
3-(1-N-BOC-amidino-4-piperidylmethyl)-5-[p-(2-methoxycarbonyl-2-N-butylsulfonylaminoethyl)phenoxy]methyloxazolidin-2-one;
with 3-(1-N-BOC-amidino-4-piperidylethyl)-5-methanesulfonyloxymethyloxazolidin-2-one
3-(1-N-BOC-amidino-4-piperidylethyl)-5-[p-(2-methoxycarbonyl-2-N-butylsulfonylaminoethyl)phenoxy]methyloxazolidin-2-one;
with 3-(1-N-BOC-amidino-4-piperidylpropyl)-5-methanesulfonyloxymethyloxazolidin-2-one
3-(1-N-BOC-amidino-4-piperidylpropyl)-5-[p-(2-methoxycarbonyl-2-N-butylsulfonylaminoethyl)phenoxy]methyloxazolidin-2-one;
with 3-(1-N-BOC-amidino-4-piperidylbutyl)-5-methanesulfonyloxymethyloxazolidin-2-one
3-(1-N-BOC-amidino-4-piperidylbutyl)-5-[p-(2-methoxycarbonyl-2-N-butylsulfonylaminoethyl)phenoxy]methyloxazolidin-2-one;
with 3-(1-isopropyl-4-piperidyl)-5-methanesulfonyloxymethyloxazolidin-2-one
3-(1-isopropyl-4-piperidyl)-5-[p-(2-methoxycarbonyl-2-N-butylsulfonylaminoethyl)phenoxy]methyloxazolidin-2-one;
with 3-(1-methyl-4-piperidylmethyl)-5-methanesulfonyloxymethyloxazolidin-2-one
3-(1-methyl-4-piperidylmethyl)-5-[p-(2-methoxycarbonyl-2-N-butylsulfonylaminoethyl)phenoxy]methyloxazolidin-2-one;
with 3-(4-N-BOC-piperazinylethyl)-5-methanesulfonyloxymethyloxazolidin-2-one
3-(4-N-BOC-piperazinylethyl)-5-[p-(2-methoxycarbonyl-2-N-butylsulfonylaminoethyl)phenoxy]methyloxazolidin-2-one;
with 3-(4-N-BOC-piperazinylpropyl)-5-methanesulfonyloxymethyloxazolidin-2-one
3-(4-N-BOC-piperazinylpropyl)-5-[p-(2-methoxycarbonyl-2-N-butylsulfonylaminoethyl)-phenoxy]methyloxazolidin-2-one;
with 3-(4-N-BOC-piperazinylbutyl)-5-methanesulfonyloxymethyloxazolidin-2-one
3-(4-N-BOC-piperazinylbutyl)-5-[p-(2-methoxycarbonyl-2-N-butylsulfonylaminoethyl)-phenoxy]methyloxazolidin-2-one;
with 3-(1-N-BOC-amidino-4-piperazinylethyl)-5-methanesulfonyloxymethyloxazolidin-2-one
3-(1-N-BOC-amidino-4-piperazinylethyl)-5-[p-(2-methoxycarbonyl-2-N-butylsulfonylaminoethyl)phenoxy]methyloxazolidin-2-one;
with 3-(1-N-BOC-amidino-4-piperazinylpropyl)-5-methanesulfonyloxymethyloxazolidin-2-one
3-(1-N-BOC-amidino-4-piperazinylpropyl)-5-[p-(2-methoxycarbonyl-2-N-butylsulfonylaminoethyl)phenoxy]methyloxazolidin-2-one;
with 3-(1-N-BOC-amidino-4-piperazinylbutyl)-5-methanesulfonyloxymethyloxazolidin-2-one
3-(1-N-BOC-amidino-4-piperazinylbutyl)-5-[p-(2-methoxycarbonyl-2-N-butylsulfonylaminoethyl)phenoxy]methyloxazolidin-2-one;

Example 4

1.2 g of 3-p-amidinophenyl-5-[p-(2-methoxycarbonyl-2-N-BOC-aminoethyl)phenoxy]methyloxazolidin-2-one [obtainable according to Ex. 1] are suspended in 60 ml of methanol, and the mixture is treated with 4 ml of 2 N NaOH solution and stirred at room temperature for 4 hours. After removal of the solvent, the residue is taken up in water, the pH is adjusted to 3 by addition of dilute HCl and the mixture is extracted with dichloromethane. The organic phase is separated and is filtered through an acidic ion exchanger. The filtrate is dried over MgSO$_4$. After removal of the solvent and additional lyophilization, 3-p-amidinophenyl-5-[p-(2-carboxy-2-N-BOC-aminoethyl)phenoxy] methyloxazolidin-2-one is obtained.

The following are obtained analogously by hydrolysis of the products from Example 1

3-(4-N-BOC-piperidyl)-5-[p-(2-carboxy-2-N-BOC-aminoethyl)phenoxy]methyloxazolidin-2-one;
3-(4-N-BOC-piperidylmethyl)-5-[p-(2-carboxy-2-N-BOC-aminoethyl)phenoxy]methyloxazolidin-2-one;
3-(4-N-BOC-piperidylethyl)-5-[p-(2-carboxy-2-N-BOC-aminoethyl)phenoxy]methyloxazolidin-2-one;
3-(4-N-BOC-piperidylpropyl)-5-[p-(2-carboxy-2-N-BOC-aminoethyl)phenoxy]methyloxazolidin-2-one;
3-(4-N-BOC-piperidylbutyl)-5-[p-(2-carboxy-2-N-BOC-aminoethyl)phenoxy]methyloxazolidin-2-one;
3-(1-N-BOC-amidino-4-piperidyl)-5-[p-(2-carboxy-2-N-BOC-aminoethyl)phenoxy]methyloxazolidin-2-one;
3-(1-N-BOC-amidino-4-piperidylmethyl)-5-[p-(2-carboxy-2-N-BOC-aminoethyl)phenoxy]methyloxazolidin-2-one;
3-(1-N-BOC-amidino-4-piperidylethyl)-5-[p-(2-carboxy-2-N-BOC-aminoethyl)phenoxy]methyloxazolidin-2-one;
3-(1-N-BOC-amidino-4-piperidylpropyl)-5-[p-(2-carboxy-2-N-BOC-aminoethyl)phenoxy]methyloxazolidin-2-one;
3-(1-N-BOC-amidino-4-piperidylbutyl)-5-[p-(2-carboxy-2-N-BOC-aminoethyl)phenoxy]methyloxazolidin-2-one;
3-(1-isopropyl-4-piperidyl)-5-[p-(2-carboxy-2-N-BOC-aminoethyl)phenoxy]methyloxazolidin-2-one;
3-(1-methyl-4-piperidylmethyl)-5-[p-(2-carboxy-2-N-BOC-aminoethyl)phenoxy]methyloxazolidin-2-one;
3-(4-N-BOC-piperazinylethyl)-5-[p-(2-carboxy-2-N-BOC-aminoethyl)phenoxy]methyloxazolidin-2-one;
3-(4-N-BOC-piperazinylpropyl)-5-[p-(2-carboxy-2-N-BOC-aminoethyl)phenoxy]methyloxazolidin-2-one;
3-(4-N-BOC-piperazinylbutyl)-5-[p-(2-carboxy-2-N-BOC-aminoethyl)phenoxy]methyloxazolidin-2-one;
3-(1-N-BOC-amidino-4-piperazinylethyl)-5-[p-(2-carboxy-2-N-BOC-aminoethyl)phenoxy]methyloxazolidin-2-one;
3-(1-N-BOC-amidino-4-piperazinylpropyl)-5-[p-(2-carboxy-2-N-BOC-aminoethyl)phenoxy]methyloxazolidin-2-one.
3-(1-N-BOC-amidino-4-piperazinylbutyl)-5-[p-(2-carboxy-2-N-BOC-aminoethyl)phenoxy]methyloxazolidin-2-one.

Example 5

0.6 g of 3-p-N-BOC-amidinophenyl-5-[p-(2-carboxy-2-N-BOC-aminoethyl)phenoxy]methyloxazolidin-2-one [obtainable according to Ex. 4] is suspended in 40 ml of 2 N HCl solution based on dioxane and stirred for 3 hours at room temperature. After removal of the solvent and customary working up, 3-p-amidinophenyl-5-[p-(2-carboxy-2-aminoethyl)phenoxy]methyloxazolidin-2-one, dihydrochloride, m.p. 165° (dec.) is obtained.

The following are obtained analogously after removal of the BOC protective group of the products from Example 4
3-(4-piperidyl)-5-[p-(2-carboxy-2-aminoethyl)phenoxy]-methyloxazolidin-2-one, dihydrochloride;
3-(4-piperidylmethyl)-5-[p-(2-carboxy-2-aminoethyl)phenoxy]methyloxazolidin-2-one, dihydrochloride;
3-(4-piperidylethyl)-5-[p-(2-carboxy-2-aminoethyl)phenoxy]methyloxazolidin-2-one, dihydrochloride;
3-(4-piperidylpropyl)-5-[p-(2-carboxy-2-aminoethyl)phenoxy]methyloxazolidin-2-one, dihydrochloride;
3-(4-piperidylbutyl)-5-[p-(2-carboxy-2-aminoethyl)phenoxy]methyloxazolidin-2-one, dihydrochloride;
3-(1-amidino-4-piperidyl)-5-[p-(2-carboxy-2-amino-ethyl)phenoxy]methyloxazolidin-2-one, dihydrochloride;
3-(1-amidino-4-piperidylmethyl)-5-[p-(2-carboxy-2-aminoethyl)phenoxy]methyloxazolidin-2-one, dihydrochloride;
3-(1-amidino-4-piperidylethyl)-5-[p-(2-carboxy-2-aminoethyl)phenoxy]methyloxazolidin-2-one, dihydrochloride;
3-(1-amidino-4-piperidylpropyl)-5-[p-(2-carboxy-2-aminoethyl)phenoxy]methyloxazolidin-2-one, dihydrochloride;
3-(1-amidino-4-piperidylbutyl)-5-[p-(2-carboxy-2-aminoethyl)phenoxy]methyloxazolidin-2-one, dihydrochloride;
3-(1-isopropyl-4-piperidyl)-5-[p-(2-carboxy-2-aminoethyl)phenoxy]methyloxazolidin-2-one, dihydrochloride;
3-(1-methyl-4-piperidylmethyl)-5-[p-(2-carboxy-2-aminoethyl)phenoxy]methyloxazolidin-2-one, dihydrochloride;
3-(4-piperazinylethyl)-5-[p-(2-carboxy-2-amino-ethyl)phenoxy]methyloxazolidin-2-one, dihydrochloride;
3-(4-piperazinylpropyl)-5-[p-(2-carboxy-2-amino-ethyl)phenoxy]methyloxazolidin-2-one, dihydrochloride;
3-(4-piperazinylbutyl)-5-[p-(2-carboxy-2-amino-ethyl)phenoxy]methyloxazolidin-2-one, dihydrochloride;
3-(1-amidino-4-piperazinylethyl)-5-[p-(2-carboxy-2-aminoethyl)phenoxy]methyloxazolidin-2-one, dihydrochloride;
3-(1-amidino-4-piperazinylpropyl)-5-[p-(2-carboxy-2-aminoethyl)phenoxy]methyloxazolidin-2-one, dihydrochloride;
3-(1-amidino-4-piperazinylbutyl)-5-[p-(2-carboxy-2-aminoethyl)phenoxy]methyloxazolidin-2-one, dihydrochloride.

Example 6

0.6 g of 3-p-N-BOC-amidinophenyl-5-[p-(2-methoxycarbonyl-2-N-BOC-aminoethyl)phenoxy]methyloxazolidin-2-one [obtainable according to Ex. 1] is suspended in 40 ml of 2 N HCl solution based on dioxane and stirred for 3 hours at room temperature. After removal of the solvent and customary working up, 3-p-amidinophenyl-5-[p-(2-methoxycarbonyl-2-aminoethyl)phenoxy]methyloxazolidin-2-one, dihydrochloride, m.p. 132–133°, is obtained.

The following are obtained analogously after removal of the BOC protective group of the products from Example 1
3-(4-piperidyl)-5-[p-(2-methoxycarbonyl-2-aminoethyl)phenoxy]methyloxazolidin-2-one, dihydrochloride;
3-(4-piperidylmethyl)-5-[p-(2-methoxycarbonyl-2-aminoethyl)phenoxy]methyloxazolidin-2-one, dihydrochloride;
3-(4-piperidylethyl)-5-[p-(2-methoxycarbonyl-2-aminoethyl)phenoxy]methyloxazolidin-2-one, dihydrochloride;
3-(4-piperidylpropyl)-5-[p-(2-methoxycarbonyl-2-aminoethyl)phenoxy]methyloxazolidin-2-one, dihydrochloride;
3-(4-piperidylbutyl)-5-[p-(2-methoxycarbonyl-2-aminoethyl)phenoxy]methyloxazolidin-2-one, dihydrochloride;
3-(1-amidino-4-piperidyl)-5-[p-(2-methoxycarbonyl-2-aminoethyl)phenoxy]methyloxazolidin-2-one, dihydrochloride;
3-(1-amidino-4-piperidylmethyl)-5-[p-(2-methoxycarbonyl-2-aminoethyl)phenoxy]methyloxazolidin-2-one, dihydrochloride;
3-(1-amidino-4-piperidylethyl)-5-[p-(2-methoxycarbonyl-2-aminoethyl)phenoxy]methyloxazolidin-2-one, dihydrochloride;

3-(1-amidino-4-piperidylpropyl)-5-[p-(2-methoxycarbonyl-2-aminoethyl)phenoxy]methyloxazolidin-2-one, dihydrochloride;

3-(1-amidino-4-piperidylbutyl)-5-[p-(2-methoxycarbonyl-2-aminoethyl)phenoxy]methyloxazolidin-2-one, dihydrochloride;

3-(1-isopropyl-4-piperidyl)-5-[p-(2-methoxycarbonyl-2-aminoethyl)phenoxy]methyloxazolidin-2-one, dihydrochloride;

3-(1-methyl-4-piperidylmethyl)-5-[p-(2-methoxycarbonyl-2-aminoethyl)phenoxy]methyloxazolidin-2-one, dihydrochloride;

3-(4-piperazinylethyl)-5-[p-(2-methoxycarbonyl-2-aminoethyl)phenoxy]methyloxazolidin-2-one, dihydrochloride;

3-(4-piperazinylpropyl)-5-[p-(2-methoxycarbonyl-2-aminoethyl)phenoxy]methyloxazolidin-2-one, dihydrochloride;

3-(4-piperazinylbutyl)-5-[p-(2-methoxycarbonyl-2-aminoethyl)phenoxy]methyloxazolidin-2-one, dihydrochloride;

3-(1-amidino-4-piperazinylethyl)-5-[p-(2-methoxycarbonyl-2-aminoethyl)phenoxy]methyloxazolidin-2-one, dihydrochloride;

3-(1-amidino-4-piperazinylpropyl)-5-[p-(2-methoxycarbonyl-2-aminoethyl)-phenoxy]methyloxazolidin-2-one, dihydrochloride;

3-(1-amidino-4-piperazinylbutyl)-5-[p-(2-methoxycarbonyl-2-aminoethyl)-phenoxy]methyloxazolidin-2-one, dihydrochloride;

Example 7

Analogously to Example 4, starting from 3-(1-N-BOC-amidino-4-piperidyl)-5-[p-(2-methoxycarbonyl-2-N-butylsulfonylaminoethyl)-phenoxy]methyloxazolidin-2-one [obtainable according to Ex. 3], 3-(1-N-BOC-amidino-4-piperidyl]-5-[p-(2-carboxy-2-N-butylsulfonylaminoethyl)phenoxy]methyloxazolidin-2-one is obtained by hydrolysis.

The following are obtained analogously by hydrolysis of 3-(4-N-BOC-piperidyl)-5-[p-(2-methoxy-carbonyl-2-N-butylsulfonylaminoethyl)phenoxy]methyloxazolidin-2-one:

3-(4-N-BOC-piperidyl)-5-[p-(2-carboxy-2-N-butylsulfonylaminoethyl)phenoxy]methyloxazolidin-2-one;

of 3-(4-N-BOC-piperidylmethyl)5-[p-(2-methoxycarbonyl-2-N-butylsulfonyl-aminoethyl)phenoxy]methyloxazolidin-2-one:

3-(4-N-BOC-piperidylmethyl)-5-[p-(2-carboxy-2-N-butylsulfonylaminoethyl)phenoxy]methyloxazolidin-2-one;

of 3-(4-N-BOC-piperidylethyl)-5-[p(2-methoxycarbonyl-2-N-butylsulfonylaminoethyl)phenoxy]methyloxazolidin-2-one:

3-(4-N-BOC-piperidylethyl)-5-[p-(2-carboxy-2-N-butylsulfonylaminoethyl)phenoxy]methyloxazolidin-2-one;

of 3-(4-N-BOC-piperidylpropyl)-5-[p-(2-methoxycarbonyl-2-N-butylsulfonylaminoethyl)phenoxy]methyloxazolidin-2-one:

3-(4-N-BOC-piperidylpropyl)-5-[p-(2-carboxy-2-N-butylsulfonylaminoethyl)phenoxy]methyloxazolidin-2-one;

of 3-(4-N-BOC-piperidylbutyl)-5-[p-(2-methoxycarbonyl-2-N-butylsulfonylaminoethyl)phenoxy]methyloxazolidin-2-one:

3-(4-N-BOC-piperidylbutyl)-5-[p-(2-carboxy-2-N-butylsulfonylaminoethyl)phenoxy]methyloxazolidin-2-one;

of 3-(1-ethyl-4-piperidyl)-5-[p-(2-methoxycarbonyl-2-N-butylsulfonylaminoethyl)phenoxy]methyloxazolidin-2-one:

3-(1-ethyl-4-piperidyl)-5-[p-(2-carboxy-2-N-butylsulfonylaminoethyl)phenoxy]methyloxazolidin-2-one;

of 3-(1-N-BOC-amidino-4-piperidylmethyl)-5-[p-(2-methoxycarbonyl-2-N-butylsulfonylaminoethyl)phenoxy]methyloxazolidin-2-one:

3-(1-N-BOC-amidino-4-piperidylmethyl)-5-[p-(2-carboxy-2-N-butylsulfonylaminoethyl)phenoxy]methyloxazolidin-2-one;

of 3-(1-N-BOC-amidino-4-piperidylethyl)-5-[p-(2-methoxycarbonyl-2-N-butylsulfonylaminoethyl)phenoxy]methyloxazolidin-2-one:

3-(1-N-BOC-amidino-4-piperidylethyl)-5-[p-(2-carboxy-2-N-butylsulfonylaminoethyl)phenoxy]methyloxazolidin-2-one;

of 3-(1-N-BOC-amidino-4-piperidylpropyl)-5-[p-(2-methoxycarbonyl-2-N-butylsulfonylaminoethyl)-phenoxy]methyloxazolidin-2-one:

3-(1-N-BOC-amidino-4-piperidylpropyl)-5-[p-(2-carboxy-2-N-butylsulfonylaminoethyl)phenoxy]methyloxazolidin-2-one;

of 3-(1-N-BOC-amidino-4-piperidylbutyl)-5-[p-(2-methoxycarbonyl-2-N-butylsulfonylaminoethyl)phenoxy]methyloxazolidin-2-one:

3-(1-N-BOC-amidino-4-piperidylbutyl)-5-[p-(2-carboxy-2-N-butylsulfonylaminoethyl)phenoxy]methyloxazolidin-2-one;

of 3-(1-isopropyl-4-piperidyl)-5-[p-(2-methoxycarbonyl-2-N-butylsulfonylaminoethyl)phenoxy]-methyloxazolidin-2-one:

3-(1-isopropyl-4-piperidyl)-5-[p-(2-carboxy-2-N-butylsulfonylaminoethyl)phenoxy]methyloxazolidin-2-one;

of 3-(1-methyl-4-piperidylmethyl)-5-[p-(2-methoxycarbonyl-2-N-butylsulfonylaminoethyl)phenoxy]methyloxazolidin-2-one:

3-(1-methyl-4-piperidylmethyl)-5-[p-(2-carboxy-2-N-butylsulfonylaminoethyl)phenoxy]methyloxazolidin-2-one;

of 3-(4-N-BOC-piperazinylethyl)-5-[p-(2-methoxycarbonyl-2-N-butylsulfonylaminoethyl)phenoxy]methyloxazolidin-2-one:

3-(4-N-BOC-piperazinylethyl)-5-[p-(2-carboxy-2-N-butylsulfonylaminoethyl)phenoxy]methyloxazolidin-2-one;

of 3-(4-N-BOC-piperazinylpropyl)-5-[p-(2-methoxycarbonyl-2-N-butylsulfonylaminoethyl)phenoxy]methyloxazolidin-2-one:

3-(4-N-BOC-piperazinylpropyl)-5-[p-(2-carboxy-2-N-butylsulfonylaminoethyl)phenoxy]methyloxazolidin-2-one;

of 3-(4-N-BOC-piperazinylbutyl)-5-[p-(2-methoxycarbonyl-2-N-butylsulfonylaminoethyl)phenoxy]methyloxazolidin-2-one:

3-(4-N-BOC-piperazinylbutyl)-5-[p-(2-carboxy-2-N-butylsulfonylaminoethyl)phenoxy]methyloxazolidin-2-one;

of 3-(1-N-BOC-amidino-4-piperazinylethyl)-5-[p-(2-methoxycarbonyl-2-N-butylsulfonylaminoethyl)phenoxy]methyloxazolidin-2-one:

3-(1-N-BOC-amidino-4-piperazinylethyl)-5-[p-(2-carboxy-2-N-butylsulfonylaminoethyl)phenoxy]methyloxazolidin-2-one;

of 3-(1-N-BOC-amidino-4-piperazinylpropyl)-5-[p-(2-methoxycarbonyl-2-N-butylsulfonylaminoethyl)phenoxy]methyloxazolidin-2-one:

3-(1-N-BOC-amidino-4-piperazinylpropyl)-5-[p-(2-carboxy-2-N-butylsulfonylaminoethyl)phenoxy]methyloxazolidin-2-one;

of 3-(1-N-BOC-amidino-4-piperazinylbutyl)-5-[p-(2-methoxycarbonyl-2-N-butylsulfonylaminoethyl)phenoxy]methyloxazolidin-2-one:

3-(1-N-BOC-amidino-4-piperazinylbutyl)-5-[p-(2-carboxy-2-N-butylsulfonylaminoethyl)phenoxy]methyloxazolidin-2-one.

Example 8

20 ml of 20% NaOH solution are added to a solution of 0.6 g of 3-p-amidinophenyl-5-[p-(2-methoxycarbonyl-2-N-BOC-aminoethyl)phenoxy]methyloxazolidin-2-one in 20 ml of THF and the mixture is stirred for 24 hours at room temperature. After removal of the solvent and freeze-drying, 3-p-amidinophenyl-5-[p-(2-carboxy-2-N-BOC-aminoethyl)phenoxy]methyloxazolidin-2-one Na salt, m.p. 120–121°, is obtained.

The following are obtained analogously 3-p-aminomethylphenyl-5-[p-(2-carboxy-2-N-BOC-aminoethyl)phenoxy]methyloxazolidin-2-one Na salt;

3-p-amidinophenyl-5-[p-(2-carboxy-2-N-butylsulfonylaminoethyl)phenoxy]methyloxazolidin-2-one Na salt;

3-p-aminomethylphenyl-5-[p-(2-carboxy-2-N-butylsulfonylaminoethyl)phenoxy]methyloxazolidin-2-one Na salt.

Example 9

A solution of 0.2 g of 1-amidino-3,5-dimethylpyrazole nitrate in 17 ml of dioxane and 5 ml of water is treated with 0.17 ml of ethyldiisopropylamine and stirred for 15 min. 0.4 g of 3-p-aminomethylphenyl-5-[p-(2-methoxycarbonyl-2-N-BOC-aminoethyl)-phenoxy]methyloxazolidin-2-one are then added, and the mixture is boiled for 30 hours, evaporated and worked up in the customary manner. 3-p-Guanidinomethylphenyl-5-[p-(2-methoxycarbonyl-2-N-BOC-aminoethyl)phenoxy]methyloxazolidin-2-one is obtained.

The following are obtained analogously from 3-m-aminomethylphenyl-5-[p-(2-methoxycarbonyl-2-N-BOC-aminoethyl)phenoxy]methyloxazolidin-2-one 3-m-guanidinomethylphenyl-5-[p-(2-methoxycarbonyl-2-N-BOC-aminoethyl)phenoxy]methyloxazolidin-2-one;

from 3-m-aminomethylphenyl-5-[p-(2-methoxycarbonyl-2-N-butylsulfonylaminoethyl)phenoxy]methyloxazolidin-2-one;

3-m-guanidinomethylphenyl-5-[p-(2-methoxycarbonyl-2-N-butylsulfonylaminoethyl)phenoxy]methyloxazolidin-2-one;

from 3-p-aminomethylphenyl-5-[p-(2-methoxycarbonyl-2-N-butylsulfonylaminoethyl)phenoxy]methyloxazolidin-2-one 3-p-guanidinomethylphenyl-5-[p-(2-methoxycarbonyl-2-N-butylsulfonylaminoethyl)phenoxy]methyloxazolidin-2-one;

from 3-o-aminomethylphenyl-5-[p-(2-methoxycarbonyl-2-N-butylsulfonylaminoethyl)phenoxy]methyloxazolidin-2-one 3-o-guanidinomethylphenyl-5-[p-(2-methoxycarbonyl-2-N-butylsulfonylaminoethyl)phenoxy]methyloxazolidin-2-one;

from 3-o-aminomethylphenyl-5-[p-(2-methoxycarbonyl-2-N-BOC-aminoethyl)phenoxy]methyloxazolidin-2-one 3-o-guanidinomethylphenyl-5-[p-(2-methoxycarbonyl-2-N-BOC-aminoethyl)phenoxy]methyloxazolidin-2-one.

Example 10

$H_2S$ gas is passed into a solution of 1.2 g of 3-p-cyanophenyl-5-[p-(2-methoxycarbonyl-2-N-butylsulfonylaminoethyl)phenoxy]methyloxazolidin-2-one [obtainable according to Ex. 1 by reaction of methyl 2-N-butylsulfonylamino-3-(4-hydroxyphenyl)propanoate with 3-p-cyanophenyl-5-methanesulfonyloxymethyloxazolidin-2-one] in 50 ml of pyridine and 7 ml of triethylamine at –10° until it is saturated. The mixture is then stirred for 14 hours at room temperature and evaporated, the residue is dissolved in 50 ml of acetone and the solution is treated with 9 ml of methyl iodide. After the mixture has again been stirred for 6 hours, the solid is filtered off, the residue is washed with 5 ml of acetone and dissolved in 30 ml of methanol, 4.6 g of ammonium acetate are added and the mixture is stirred for 24 hours at room temperature. After customary working up, 3-p-amidinophenyl-5-[p-(2-methoxycarbonyl-2-N-butylsulfonylaminoethyl)phenoxy]methyloxazolidin-2-one, m.p. 162–163°, is obtained.

The following are obtained analogously from 3-m-cyanophenyl-5-[p-(2-methoxycarbonyl-2-N-butylsulfonylaminoethyl)phenoxy]methyloxazolidin-2-one 3-m-amidinophenyl-5-[p-(2-methoxycarbonyl-2-N-butylsulfonylaminoethyl)phenoxy]methyloxazolidin-2-one;

from 3-p-cyanophenyl-5-[p-(2-methoxycarbonyl-2-N-BOC-aminoethyl)phenoxy]methyloxazolidin-2-one 3-p-amidinophenyl-5-[p-(2-methoxycarbonyl-2-N-BOC-aminoethyl)phenoxy]methyloxazolidin-2-one, m.p.159–160°;

from 3-p-cyanophenyl-5-[p-(2-methoxycarbonyl-2-N-p-toluenesulfonylaminoethyl)phenoxy]methyloxazolidin-2-one 3-p-amidinophenyl-5-[p-(2-methoxycarbonyl-2-N-p-toluenesulfonylaminoethyl)phenoxy]methyloxazolidin-2-one;

from 3-m-cyanophenyl-5-[p-(2-methoxycarbonyl-2-N-p-toluenesulfonylaminoethyl)phenoxy]methyloxazolidin-2-one 3-m-amidinophenyl-5-[p-(2-methoxycarbonyl-2-N-p-toluenesulfonylaminoethyl)phenoxy]methyloxazolidin-2-one.

Example 11

Analogously to Example 4, starting from 3-p-amidinophenyl-5-[p-(2-methoxycarbonyl-2-butylsulfonylaminoethyl)phenoxy]methyloxazolidin-2-one [obtainable according to Ex. 10], 3-p-amidinophenyl-5-[p-(2-carboxy-2-N-butylsulfonylaminoethyl)phenoxy]methyloxazolidin-2-one, m.p. 236–237°, is obtained by hydrolysis.

The following are analogously obtained by hydrolysis of 3-m-amidinophenyl-5-[p-(2-methoxycarbonyl-2-N-butylsulfonylaminoethyl)phenoxy]methyloxazolidin-2-one 3-m-amidinophenyl-5-[p-(2-carboxy-2-N-butylsulfonylaminoethyl)phenoxy]methyloxazolidin-2-one;

of 3-p-amidinophenyl-5-[p-(2-methoxycarbonyl-2-N-p-toluenesulfonylaminoethyl)phenoxy]methyloxazolidin-2-one 3-p-amidinophenyl-5-[p-(2-carboxy-2-N-p-toluenesulfonylaminoethyl)phenoxy]methyloxazolidin-2-one;

of 3-m-amidinophenyl-5-[p-(2-methoxycarbonyl-2-N-p-toluenesulfonylaminoethyl)phenoxy]methyloxazolidin-2-one 3-m-amidinophenyl-5-[p-(2-carboxy-2-N-p-toluenesulfonylaminoethyl)phenoxy]methyloxazolidin-2-one.

Example 12

1.37 g of 3-p-(5-oxo-1,2,4-oxadiazolin-3-yl)phenyl-5-[p-(2-methoxycarbonyl-2-N-ethylaminoethyl)phenoxy]methyloxazolidin-2-one [obtainable according to Ex. 1 by reaction of methyl 2-N-ethylamino-3-(4-hydroxyphenyl)propanoate with 3-p-(5-oxo-1,2,4-oxadiazolin-3 -yl)phenyl-5-methanesulfonylmethyloxazolidin-2-one] are dissolved in 50 ml of methanol and hydrogenated on Raney nickel. The reaction mixture is then filtered and the filtrate is concentrated in vacuo. The product obtained is treated with 20 ml of ethyl acetate in the presence of heat and the product is filtered off with suction after cooling. 3-p-Amidinophenyl-5-[p-(2-methoxycarbonyl-2-N-ethylaminoethyl)phenoxy]methyloxazolidin-2-one is obtained.

The following are obtained analogously by reductive cleavage of the 5-oxo-1,2,4-oxadiazoline group from 3-p-(5-oxo-1,2,4-oxadiazolin-3-yl)phenyl-5-[p-(2-methoxycarbonyl-2-N-isopropylaminoethyl)phenoxy]methyloxazolidin-2-one 3-p-amidinophenyl-5-[p-(2-methoxycarbonyl-2-N-isopropylaminoethyl)phenoxy]methyloxazolidin-2-one;

from 3-p-(5-oxo-1,2,4-oxadiazolin-3-yl)phenyl-5-[p-(2-methoxycarbonyl-2-N-acetylaminoethyl)phenoxy]methyloxazolidin-2-one 3-p-amidinophenyl-5-[p-(2-methoxycarbonyl-2-N-acetylaminoethyl)phenoxy]methyloxazolidin-2-one;

from 3-p-(5-oxo-1,2,4-oxadiazolin-3-yl)phenyl-5-[p-(2-methoxycarbonyl-2-N-propionylaminoethyl)phenoxy]methyloxazolidin-2-one 3-p-amidinophenyl-5-[p-(2-methoxycarbonyl-2-N-propionylaminoethyl)phenoxy]methyloxazolidin-2-one;

from 3-p-(5-oxo-1,2,4-oxadiazolin-3-yl)phenyl-5-[p-(2-methoxycarbonyl-2-N-BOC-aminoethyl)phenoxy]methyloxazolidin-2-one 3-p-amidinophenyl-5-[p-(2-methoxycarbonyl-2-N-BOC-aminoethyl)phenoxy]methyloxazolidin-2-one;

from 3-p-(5-oxo-1,2,4-oxadiazolin-3-yl)phenyl-5-[p-(2-methoxycarbonyl-2-N-tert-butylaminoethyl)phenoxy]methyloxazolidin-2-one 3-p-amidinophenyl-5-[p-(2-methoxycarbonyl-2-5N-tert-butylaminoethyl)phenoxy]methyloxazolidin-2-one.

Example 13

Analogously to Example 4, the following carboxylic acids are obtained from Example 12 by hydrolysis of the corresponding esters:

3-p-amidinophenyl-5-[p-(2-carboxy-2-N-ethylaminoethyl)phenoxy]methyloxazolidin-2-one;
3-p-amidinophenyl-5-[p-(2-carboxy-2-N-isopropylaminoethyl)phenoxy]methyloxazolidin-2-one;
3-p-amidinophenyl-5-[p-(2-carboxy-2-N-acetylaminoethyl)-phenoxy]methyloxazolidin-2-one;
3-p-amidinophenyl-5-[p-(2-carboxy-2-N-propionylaminoethyl)phenoxy]methyloxazolidin-2-one;
3-p-amidinophenyl-5-[p-(2-carboxy-2-N-BOC-aminoethyl)phenoxy]methyloxazolidin-2-one;
3-p-amidinophenyl-5-[p-(2-carboxy-2-N-tert-butylaminoethyl)phenoxy]methyloxazolidin-2-one.

Example 14

Analogously to Example 4, the following carboxylic acids are obtained from Example 9 by hydrolysis of the corresponding esters:

3-p-guanidinomethylphenyl-5-[p-(2-carboxy- 2-N-BOC-aminoethyl)phenoxy]methyloxazolidin-2-one;
3-m-guanidinomethylphenyl-5-[p-(2-carboxy-2-N-BOC-aminoethyl)phenoxy]methyloxazolidin-2-one;
3-m-guanidinomethylphenyl-5-[p-(2-carboxy-2-N-butylsulfonylaminoethyl)phenoxy]methyloxazolidin-2-one;
3-p-guanidinomethylphenyl-5-[p-(2-carboxy-2-N-butylsulfonylaminoethyl)phenoxy]methyloxazolidin-2-one;
3-o-guanidinomethylphenyl-5-[p-(2-carboxy-2-N-butylsulfonylaminoethyl)phenoxy]methyloxazolidin-2-one;
3-o-guanidinomethylphenyl-5-[p-(2-carboxy-2-N-BOC-aminoethyl)phenoxy]methyloxazolidin-2-one.

Example 15

Analogously to Example 5, the following compounds are obtained by removal of the BOC protective group starting from the products of Example 14:

3-p-guanidinomethylphenyl-5-[p-(2-carboxy-2-aminoethyl)phenoxy]methyloxazolidin-2-one;
3-m-guanidinomethylphenyl-5-[p-(2-carboxy-2-aminoethyl)phenoxy]methyloxazolidin-2-one;
3-o-guanidinomethylphenyl-5-[p-(2-carboxy-2-aminoethyl)phenoxy]methyloxazolidin-2-one.

Example 16

One equivalent of propanesulfonic acid chloride and two equivalents of triethylamine is added to a solution of 0.5 g of 3-p-(5-oxo-1,2,4-oxadiazolin-3-yl)phenyl-5-[p-(2-benzyloxycarbonyl-2-aminoethyl)phenoxy]-methyl-oxazolidin-2-one [obtainable by reaction of benzyl 2-N-BOC-amino-3-(4-hydroxyphenyl)propanoate, obtainable from tyrosine by esterification with benzyl alcohol and introduction of the BOC protective group, with 3-p-(5-oxo-1,2,4-oxadiazolin-3-yl)phenyl-5-methanesulfonyl-methyloxazolidin-2-one to give 3-p-(5-oxo-1,2,4-oxadiazolin-3-yl)phenyl-5-[p-(2-benzyloxy-carbonyl-2-N-BOC-aminoethyl)phenoxy]-methyloxazolidin-2-one, followed by treatment with trifluoro acetic acid] in 10 ml of dichloromethane. The mixture is stirred for one hour at cooling conditions. After customary working up, 3-p-(5-oxo-1,2,4-oxadiazolin-3-yl)phenyl-5-[p-(2-benzyloxycarbonyl-2-N-propanesulfonyl-aminoethyl)phenoxy]methyl-oxazolidin-2-one, FAB-MS: m/e 635 (M+H$^+$) is obtained.

The following are obtained analogously by reaction of 3-p-(5-oxo-1,2,4-oxadiazolin-3-yl)phenyl-5-[p-(2-benzyloxycarbonyl-2-aminoethyl)-phenoxy]-methyloxazolidin-2-one
with ethanesulfonic acid chloride:

3-p-(5-oxo-1,2,4-oxadiazolin-3-yl)phenyl-5-[p-(2-benzyloxy-carbonyl-2-N-ethanesulfonyl-aminoethyl)phenoxy]-methyl-oxazolidin-2-one;

with toluenesulfonic acid chloride:
   3-p-(5-oxo-1,2,4-oxadiazolin-3-yl)phenyl-5-[p-(2-benzyloxy-carbonyl-2-N-toluensulfonyl-aminoethyl)phenoxy]-methyl-oxazolidin-2-one;
with benzylsulfonic acid chloride:
   3-p-(5-oxo-1,2,4-oxadiazolin-3-yl)phenyl-5-[p-(2-benzyloxy-carbonyl-2-N-benzylsulfonyl-aminoethyl)phenoxy]-methyl-oxazolidin-2-one;
with hexanesulfonic acid chloride:
   3-p-(5-oxo-1,2,4-oxadiazolin-3-yl)phenyl-5-[p-(2-benzyloxy-carbonyl-2-N-hexanesulfonyl-aminoethyl)phenoxy]-methyl-oxazolidin-2-one;
with pentanesulfonic acid chloride:
   3-p-(5-oxo-1,2,4-oxadiazolin-3-yl)phenyl-5-[p-(2-benzyloxy-carbonyl-2-N-pentanesulfonyl-aminoethyl)phenoxy]-methyl-oxazolidin-2-one;
with hexadecanesulfonic acid chloride:
   3-p-(5-oxo-1,2,4-oxadiazolin-3-yl)phenyl-5-[p-(2-benzyloxy-carbonyl-2-N-hexadecanesulfonyl-aminoethyl)phenoxy]-methyl-oxazolidin-2-one;
with butyric chloride:
   3-p-(5-oxo-1,2,4-oxadiazolin-3-yl)phenyl-5-[p-(2-benzyloxy-carbonyl-2-N-butanoyl-aminoethyl)-phenoxy]methyl-oxazolidin-2-one;
with pentanoic chloride:
   3-p-(5-oxo-1,2,4-oxadiazolin-3-yl)phenyl-5-[p-(2-benzyloxy-carbonyl-2-N-pentanoyl-aminoethyl)-phenoxy]methyl-oxazolidin-2-one;
with hexanoic chloride:
   3-p-(5-oxo-1,2,4-oxadiazolin-3-yl)phenyl-5-[p-(2-benzyloxy-carbonyl-2-N-hexanoyl-aminoethyl)-phenoxy]methyl-oxazolidin-2-one;
with benzoic chloride:
   3-p-(5-oxo-1,2,4-oxadiazolin-3-yl)phenyl-5-[p-(2-benzyloxy-carbonyl-2-N-benzoyl-aminoethyl)-phenoxy]methyl-oxazolidin-2-one;
with 1-naphthoic chloride:
   3-p-(5-oxo-1,2,4-oxadiazolin-3-yl)phenyl-5-[p-(2-benzyloxy-carbonyl-2-N-(1-naphthoyl)-aminoethyl)phenoxy]-methyl-oxazolidin-2-one;
with 2-naphthoic chloride:
   3-p-(5-oxo-1,2,4-oxadiazolin-3-yl)phenyl-5-[p-(2-benzyloxy-carbonyl-2-N-(2-naphthoyl)-aminoethyl)phenoxy]-methyl-oxazolidin-2-one;

Example 17

For hydrolysis of the benzyl ester and cleavage of the oxadiazoline ring 0.4 g 3-p-(5-oxo-1,2,4-oxadiazolin-3-yl)phenyl-5-[p-(2-benzyloxy-carbonyl-2-N-propanesulfonyl-aminoethyl)phenoxy]-methyl-oxazolidin-2-one are dissolved in 10 ml dichloromethane, 1 ml acetic acid, 0.5 ml water and 5 ml methanol. 0.1 g Pd/C (10%) is added and the mixture is treated with hydrogen at room temperature for 30 minutes. The catalyst is filtered off and after customary working up, 3-p-amidinophenyl-5-[p-(2-carboxy-2-N-propanesulfonyl-aminoethyl)phenoxy]-methyl-oxazolidin-2-one, m.p. 200° is obtained.

The following are obtained analogously by hydrogenation of the products from Example 16
3-p-amidinophenyl-5-[p-(2-carboxy-2-N-ethanesulfonylaminoethyl)phenoxy]-methyl-oxazolidin-2-one, m.p. 212° (dec.);
3-p-amidinophenyl-5-[p-(2-carboxy-2-N-toluenesulfonylaminoethyl)phenoxy]-methyl-oxazolidin-2-one, m.p. 205° (dec.);
3-p-amidinophenyl-5-[p-(2-carboxy-2-N-benzylsulfonylaminoethyl)phenoxy]-methyl-oxazolidin-2-one, m.p. 211° (dec.);
3-p-amidinophenyl-5-[p-(2-carboxy-2-N-hexanesulfonylaminoethyl)phenoxy]-methyl-oxazolidin-2-one, m.p. 198° (dec.);
3-p-amidinophenyl-5-[p-(2-carboxy-2-N-pentanesulfonylaminoethyl)phenoxy]-methyl-oxazolidin-2-one, m.p. 215° (dec.);
3-p-amidinophenyl-5-[p-(2-carboxy-2-N-hexadecanesulfonyl-aminoethyl)phenoxy]-methyl-oxazolidin-2-one, m.p. 220° (dec.);
3-p-amidinophenyl-5-[p-(2-carboxy-2-N-butanoyaminoethyl)phenoxy]-methyl-oxazolidin-2-one, m.p. 190° (dec.);
3-p-amidinophenyl-5-[p-(2-carboxy-2-N-pentanoylaminoethyl)phenoxy]-methyl-oxazolidin-2-one, m.p. 195° (dec.);
3-p-amidinophenyl-5-[p-(2-carboxy-2-N-hexanoylaminoethyl)phenoxy]-methyl-oxazolidin-2-one, m.p. 188° (dec.);
3-p-amidinophenyl-5-[p-(2-carboxy-2-N-benzoylaminoethyl)phenoxy]-methyl-oxazolidin-2-one, m.p. 204° (dec.);
3-p-amidinophenyl-5-[p-(2-carboxy-2-N-(1-naphthoyl)aminoethyl)phenoxy]-methyl-oxazolidin-2-one;
3-p-amidinophenyl-5-[p-(2-carboxy-2-N-(2-naphthoyl)aminoethyl)phenoxy]-methyl-oxazolidin-2-one, m.p. 226° (dec.).

The following examples relate to pharmaceutical preparations:

Example A

Injection Vials

A solution of 100 g of an active compound of the formula I and 5 g of disodium hydrogen phosphate are adjusted to pH 6.5 in 3 l of double-distilled water using 2-N hydrochloric acid, sterile-filtered, filled into injection vials, lyophilized under sterile conditions and sealed aseptically. Each injection vial contains 5 mg of active compound.

Example B

Suppositories

A mixture of 20 g of an active compound of the formula I is melted with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The solution is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F

Coated Tablets

Analogously to Example E, tablets are pressed which are then coated in a customary manner with a coating of sucrose, potato starch, talc, tragacanth and colourant.

Example G

Capsules 2 kg of active compound of the formula I are filled into hard gelatin capsules in a customary manner such that each capsule contains 20 mg of the active compound.

Example H

Ampoules

A solution of 1 kg of active compound of the formula I in 60 1 of double-distilled water is sterile-filtered, filled into ampoules, lyophilized under sterile conditions and sealed aseptically. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oxazolidinone compound of formula I

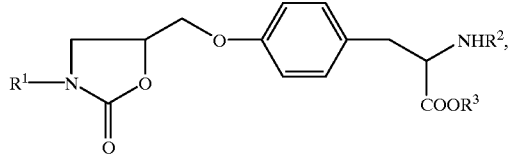

I wherein $R^1$ is

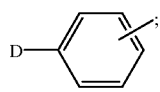

$R^2$ is H, A, Ac, A—$SO_2$—, Ar—$SO_2$— or the amino protective group, BOC;

$R^3$ is H, A, cycloalkyl having 3 to 7 C atoms, Ar or Ar—$(CH_2)_k$—;

A is alkyl having 1 to 16 C atoms;

D is $H_2N$—$CH_2$—, $H_2N$—C(=NH)— or $H_2N$—C(=NH)—NH—$CH_2$—, wherein primary amino groups in each case can optionally be provided with amino protective groups;

Ac is alkanoyl having 1 to 10 C atoms or benzoyl or napththoyl having 7 to 11 C atoms;

Ar is benzyl, unsubstituted phenyl or phenyl which is mono- or disubstituted by A, Cl, Br, I, OA, OH, $NO_2$, CN, $NH_2$, NHA, $NA_2$ or combinations thereof; and k is 2, 3 or 4; or a physiologically acceptable salt thereof.

2. A compound according to claim 1, wherein said compound is an enantiomer or a disastereomer.

3. A process for preparation of a compound according to claim 1, comprising:

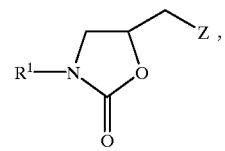

II wherein $R^1$ has the meaning given, and

Z is Cl, Br, I, OH or a reactive esterified OH group, with a compound of the formula III

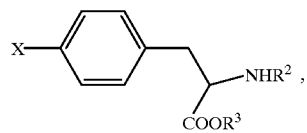

III wherein $R^2$ and $R^3$ have the meanings indicated and

X is OH or a salt-like radical derivable from OH.

4. A compound according to claim 1, wherein $R^2$ is H or A—$SO_2$—.

5. A pharmaceutical composition comprising one or more compounds according to claim 1 and a physiologically acceptable carrier.

6. A composition according to claim 5, wherein the amount of said compound is 5 mg–1 g.

7. A method of preventing development of blood platelet thrombi in a patient comprising administering to said patient an effective amount of a compound according to claim 1.

8. A method according to claim 7, wherein the daily dosage of said compound is 0.1–20 mg/kg.

* * * * *